US012031654B2

(12) United States Patent
Hartridge et al.

(10) Patent No.: US 12,031,654 B2
(45) Date of Patent: Jul. 9, 2024

(54) FLUID CONNECTOR

(71) Applicant: CYTIVA US LLC, Marlborough, MA (US)

(72) Inventors: Thomas James Hartridge, Portsmouth (GB); Davi Uliana, Portsmouth (GB); Daniel J. Kesselaar, Portsmouth (GB)

(73) Assignee: CYTIVA US LLC, Marlborough, MA (US)

( * ) Notice: Subject to any disclaimer, the term of this patent is extended or adjusted under 35 U.S.C. 154(b) by 181 days.

(21) Appl. No.: 17/563,880

(22) Filed: Dec. 28, 2021

(65) Prior Publication Data

US 2023/0204138 A1    Jun. 29, 2023

(51) Int. Cl.
| | |
|---|---|
| *F16L 37/00* | (2006.01) |
| *A61M 39/10* | (2006.01) |
| *A61M 39/22* | (2006.01) |
| *F16K 11/044* | (2006.01) |
| *F16K 27/02* | (2006.01) |
| *F16L 37/091* | (2006.01) |

(52) U.S. Cl.
CPC ........... *F16L 37/008* (2013.01); *A61M 39/10* (2013.01); *F16K 11/044* (2013.01); *F16K 27/0263* (2013.01); *F16L 37/0915* (2016.05); *A61M 2039/224* (2013.01)

(58) Field of Classification Search
CPC ........ F16K 11/20; F16K 11/22; F16K 11/207; F16K 27/003; A61M 2039/224; A61M 39/223; A61M 39/18; A61M 39/1011; A61M 39/1055; F16L 37/38; F16L 37/46; F16L 2201/44; F16L 27/093
See application file for complete search history.

(56) References Cited

U.S. PATENT DOCUMENTS

| | | | |
|---|---|---|---|
| 4,456,026 A | | 6/1984 | Kantor |
| 5,560,548 A | * | 10/1996 | Mueller ................ F16L 37/248 4/615 |
| 6,679,529 B2 | | 1/2004 | Johnson et al. |
| 6,704,946 B1 | * | 3/2004 | Mueller .................. E03C 1/023 239/447 |
| 7,488,446 B2 | | 5/2009 | Meyer et al. |
| 7,546,857 B2 | | 6/2009 | Chadbourne et al. |

(Continued)

FOREIGN PATENT DOCUMENTS

| | | |
|---|---|---|
| CN | 201568609 U | 9/2010 |
| CN | 107709866 A | 2/2018 |

(Continued)

OTHER PUBLICATIONS

IPOS, Search Report issued in Singaporean Patent Application No. 10202260043V, dated on May 25, 2023.

(Continued)

*Primary Examiner* — Zachary T Dragicevich
*Assistant Examiner* — Alexander T Rufrano
(74) *Attorney, Agent, or Firm* — Leydig, Voit & Mayer, Ltd.

(57) ABSTRACT

A connector is provided comprising first and second hollow connector bodies, the connector having a first expanded position providing a first fluid flow path through the first hollow connector body, and a second collapsed position providing a second fluid flow path through the first and second hollow connector bodies.

6 Claims, 16 Drawing Sheets

(56) References Cited

U.S. PATENT DOCUMENTS

| | | |
|---|---|---|
| 7,631,660 B2 | 12/2009 | deCler et al. |
| 9,726,308 B2 | 8/2017 | Williams et al. |
| 10,234,042 B2 | 3/2019 | Bowdery |
| 10,247,342 B2 | 4/2019 | Kesselaar |
| 10,946,183 B2 | 3/2021 | Faldt et al. |
| 11,116,957 B2 | 9/2021 | Ueda et al. |
| 2007/0102450 A1 | 5/2007 | Stiers |
| 2009/0198209 A1 | 8/2009 | Usher et al. |
| 2014/0124087 A1 | 5/2014 | Anderson et al. |
| 2017/0284584 A1 | 10/2017 | Kesselaar et al. |
| 2017/0299099 A1 | 10/2017 | Williams et al. |
| 2017/0368325 A1 | 12/2017 | Ueda |
| 2018/0296817 A1 | 10/2018 | Burdge |
| 2019/0298985 A1 | 10/2019 | Truong et al. |
| 2019/0368630 A1 | 12/2019 | Fortner et al. |
| 2020/0025310 A1 | 1/2020 | McLaughlin et al. |
| 2020/0032922 A1 | 1/2020 | Wilhelm |
| 2020/0171234 A1 | 6/2020 | Cowan et al. |
| 2020/0386330 A1 | 12/2020 | Stanton et al. |

FOREIGN PATENT DOCUMENTS

| | | |
|---|---|---|
| CN | 108030976 A | 5/2018 |
| EP | 0 639 389 A1 | 2/1995 |
| EP | 3 488 895 A1 | 5/2019 |
| EP | 3 225 895 B1 | 10/2019 |
| WO | WO 2009/097321 A1 | 8/2009 |

OTHER PUBLICATIONS

European Patent Office, Extended European Search Report issued in counterpart European Patent Application No. 22207457.7, mailed on Apr. 20, 2023.

\* cited by examiner

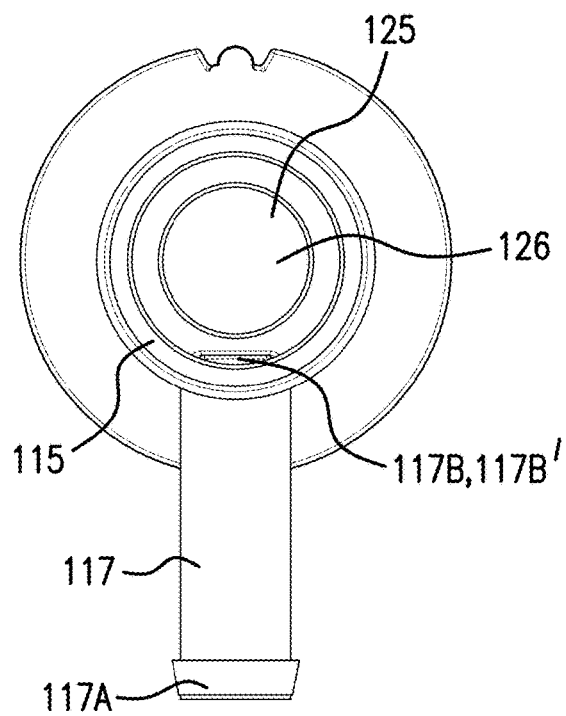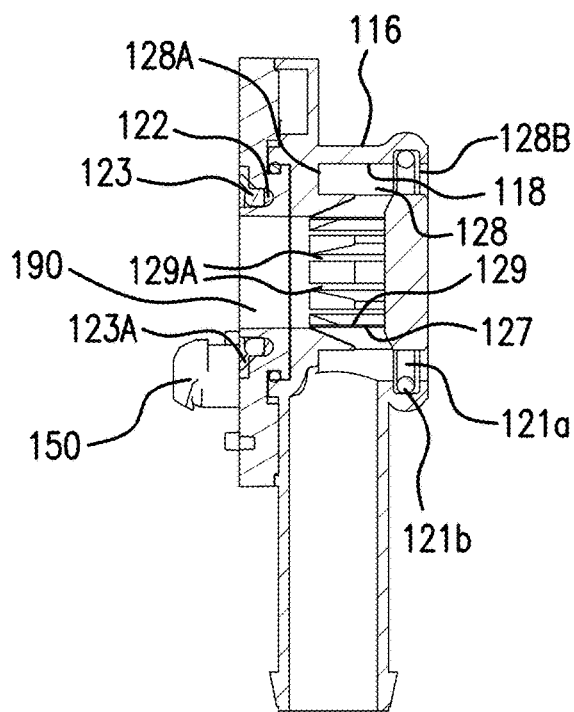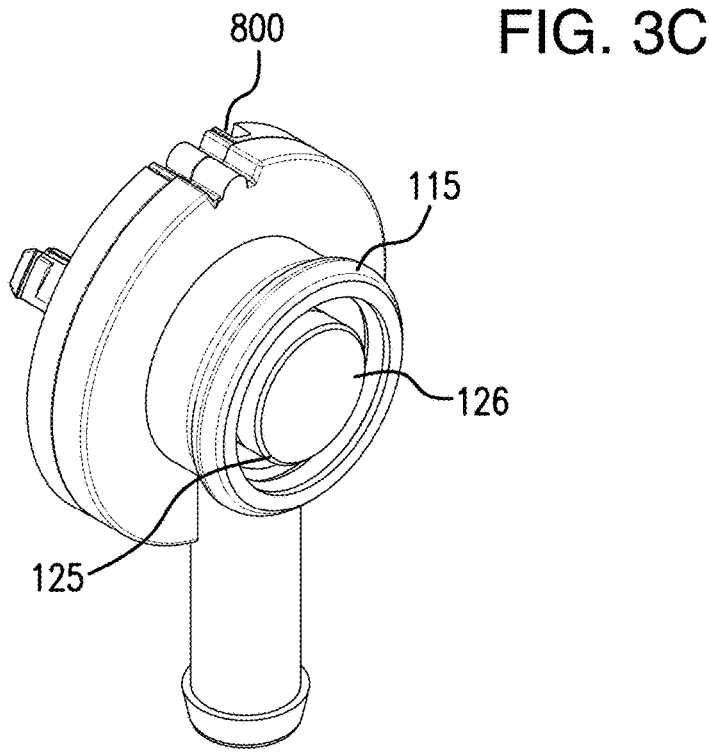
FIG. 3B
FIG. 3C
FIG. 3A

US 12,031,654 B2

FLUID CONNECTOR

BACKGROUND OF THE INVENTION

Connectors for use in fluid processing systems and fluid processing (such as liquid products used in the pharmaceutical and biotechnological industries) are known. However, there is a need for improved connectors. The present invention provides for ameliorating at least some of the disadvantages of the prior art. These and other advantages of the present invention will be apparent from the description as set forth below.

BRIEF SUMMARY OF THE INVENTION

An aspect of the invention provides a connector comprising (a) a first hollow connector body having (i) a side wall with a hollow extension having an open first end and an open second end, the open second end forming a hollow extension aperture in the side wall; (ii) an outer face with an outer face aperture; and (iii) an inner face including a first projection, the first projection having an annular inner wall, surrounding a second projection, the second projection having a second projection annular outer wall, forming a space between the annular inner wall of the first projection and the annular outer wall of the second projection, the space having a bottom wall and an open end opposite the bottom wall; the second projection having a second projection annular inner wall and slots passing through the second projection inner wall and the second projection outer wall, a closed top end and an open second end providing the outer face aperture of the first hollow connector body, the outer face aperture being in fluid communication with the slots passing through the second projection inner wall and the second projection outer wall; (b) a second hollow connector body having an inner face including a hollow projection, the hollow projection having a wall having an inner surface and an outer surface and a top end with a planar annular surface; and an outer face; the second hollow connector body having an aperture passing through the inner face, the hollow projection and the outer face; wherein the connector has a first expanded position providing a first fluid flow path through the outer face aperture, the slots, the space between the annular inner wall of the first projection and the annular outer wall of the second projection, the side wall and the hollow extension of the first hollow connector body, when the top end with the planar annular surface of the second hollow connector body is a distance from the bottom wall of the space in the first hollow connector body; and, a second collapsed position providing a second fluid flow path through the outer face aperture, the slots, and the open end opposite the bottom wall of the first hollow connector body, and through the aperture passing through the inner face, the hollow projection and the outer face of the second hollow connector body, when the top end with the planar annular surface of the second hollow connector body contacts the bottom wall of the space of the first hollow connector body.

In a preferred aspect of the connector, the outer face of the first hollow connector body includes an integrally formed locking mechanism; the integrally formed locking mechanism comprising at least one lug including a slot, and at least one ramp; and an anti-actuation assembly engagement portion comprising at least one recess and/or at least one protrusion; and, the outer face of the second hollow connector body includes an integrally formed locking mechanism; the integrally formed locking mechanism comprising at least one lug including a slot, and at least one ramp; and an anti-actuation assembly engagement portion comprising at least one recess and/or at least one protrusion.

In another aspect, a connector assembly is provided, comprising an aspect of the connector, further comprising a first removable cap, engaged with the first hollow connector body, wherein the removable anti-actuation assembly is interposed between the first removable cap and the first hollow connector body, the first removable cap covering the outer face of the first hollow connector body; and, a second removable cap, engaged with the second hollow connector body, wherein the removable anti-actuation assembly is interposed between the second removable cap and the second hollow connector body, the second removable cap covering the outer face of the second hollow connector body.

In accordance with yet other aspects of the invention, a method for making fluid connections and a method for processing fluid are provided.

BRIEF DESCRIPTION OF THE SEVERAL VIEWS OF THE DRAWING(S)

FIG. 1A is a drawing showing a cross-sectional view of a first connector comprising first and second hollow connector bodies, wherein the connector is in a first expanded position providing a first fluid flow path through the first hollow body according to an aspect of the invention (also showing anti-actuation subassemblies and peel strips connected to outer faces of first and second hollow connector bodies); FIG. 1B is a drawing showing a cross-sectional view of the connector shown in FIG. 1A in a second collapsed position providing a second fluid flow path through the first and second hollow bodies;

Figure 3D:
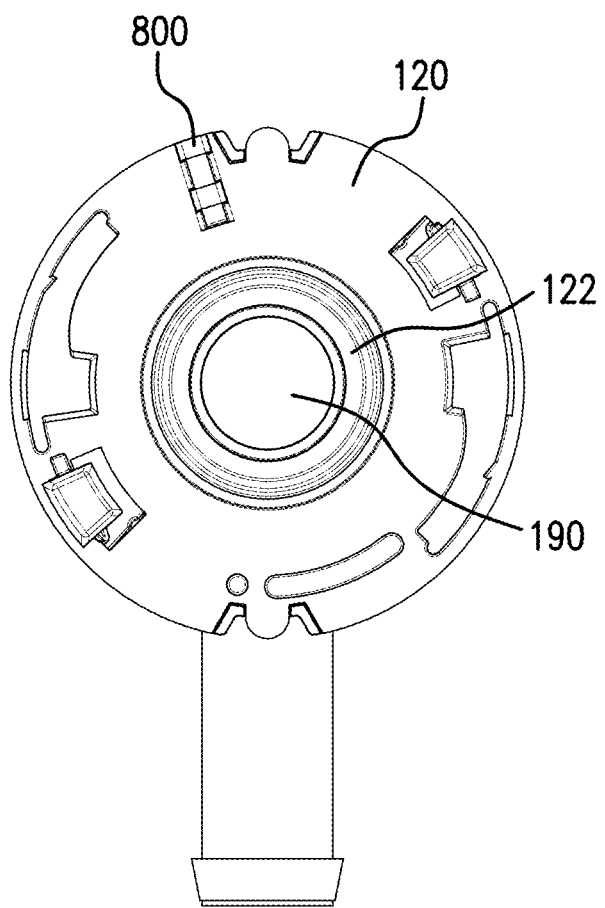

FIG. 3A is a drawing showing a perspective view of the inner face of the first connector body according to an aspect of the invention; FIG. 3B is a drawing showing the top view of the inner face of the first connector body shown in FIG. 3A; FIG. 3C is a drawing showing a cross-sectional view of the first connector body shown in FIG. 3A; FIG. 3D is a drawing showing a top view of the outer face of the first connector body shown in FIG. 3A.

Figure 4:
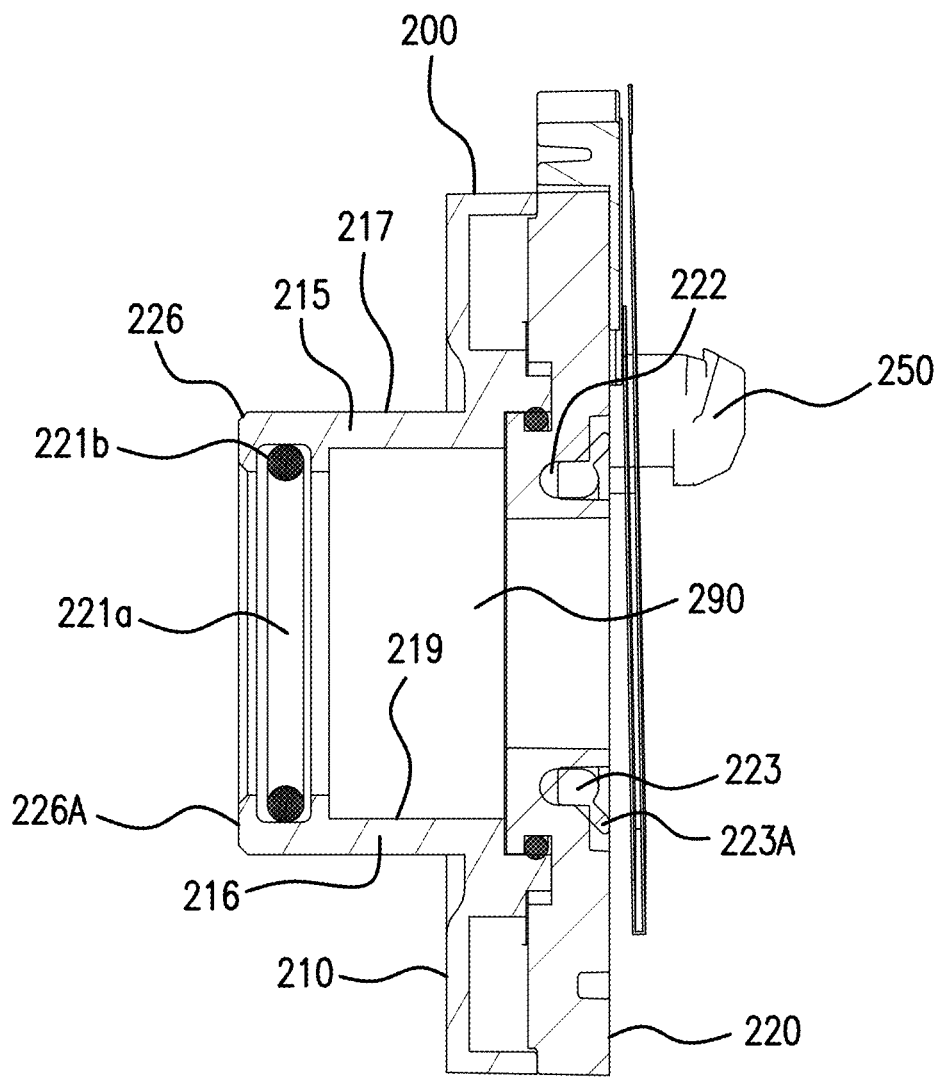

FIG. 4 is a drawing showing a cross-sectional view of the second hollow body.

Figure 2A:
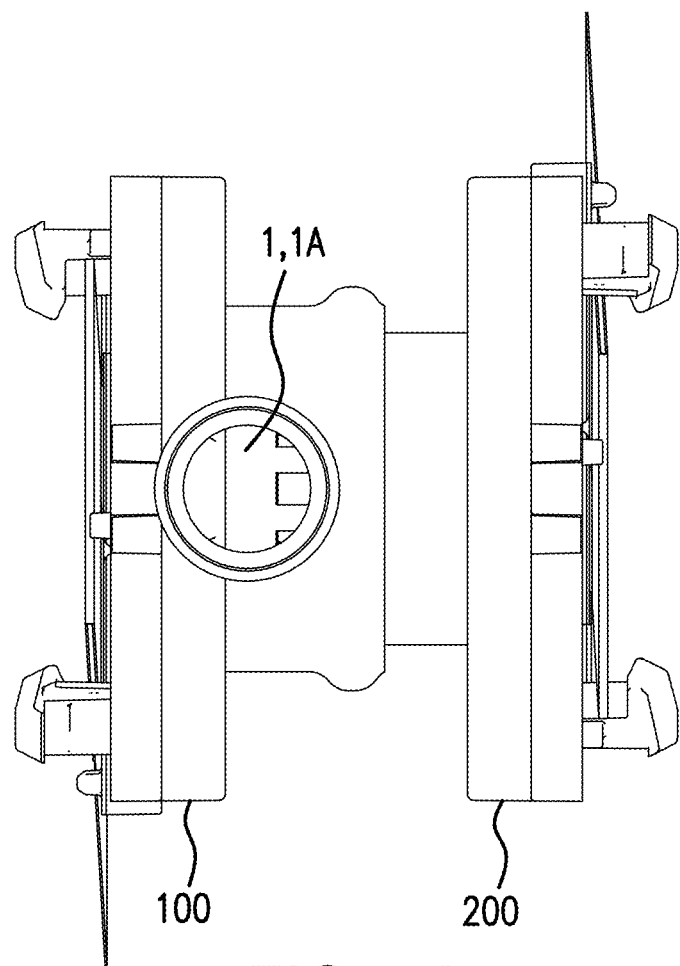
FIG. 2A is a drawing showing a side perspective view of the first connector in the first expanded position shown in FIG. 1A.
Figure 2B:
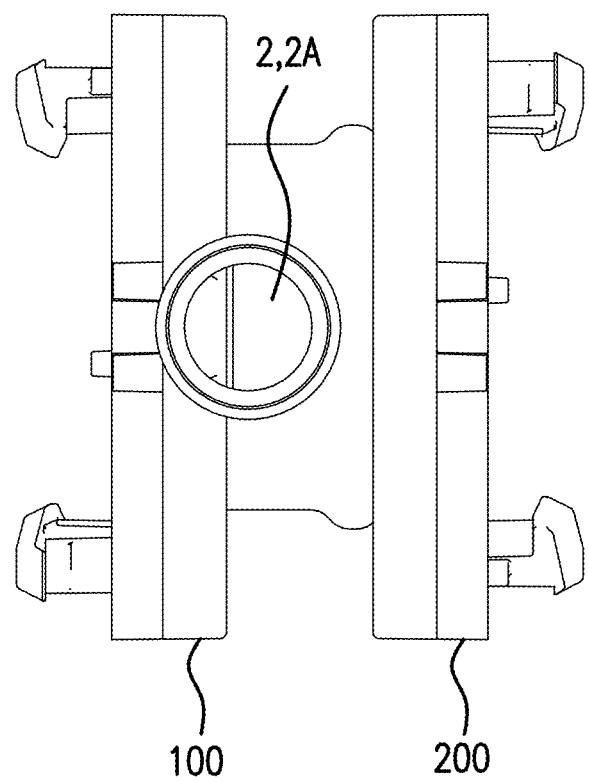
FIG. 2B is a drawing showing a side perspective view of the first connector in the second collapsed position shown in FIG. 1B.
Figure 2C:
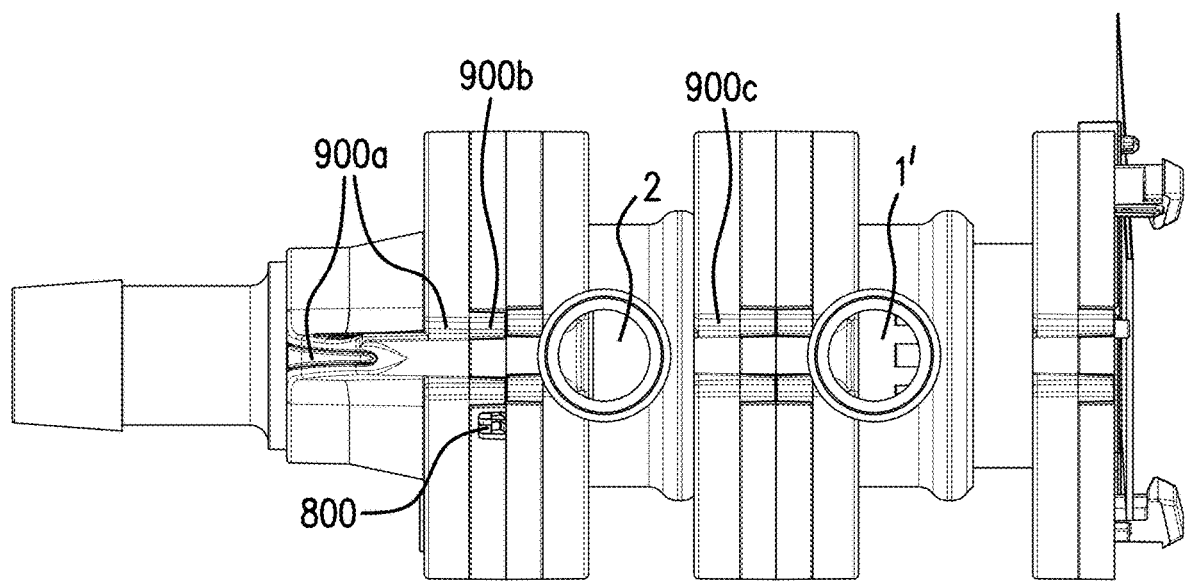
FIG. 2C is a drawing showing a side perspective view of the joined first and second connectors shown in FIG. 1C.
Figure 5A:
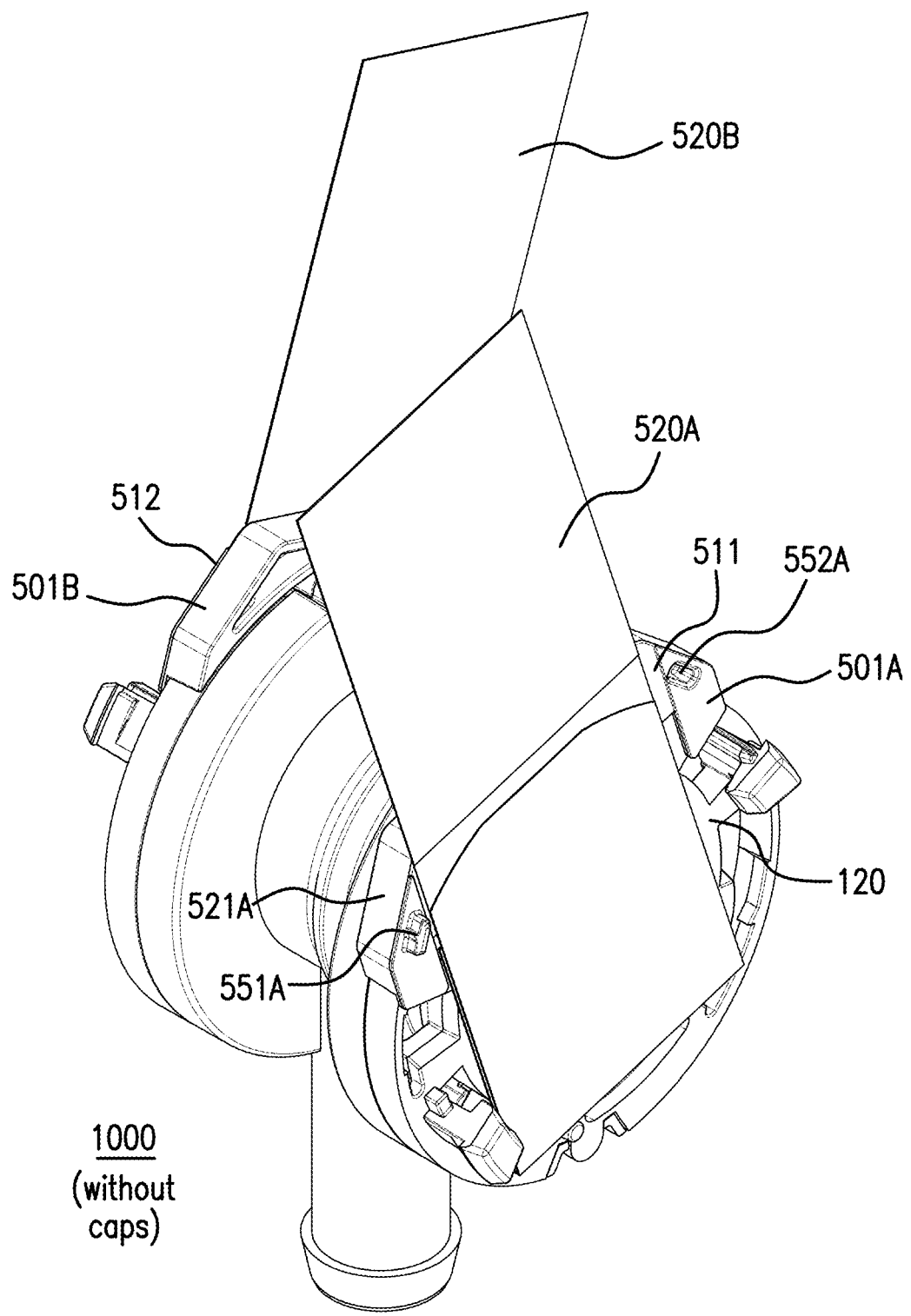
Figure 5B:
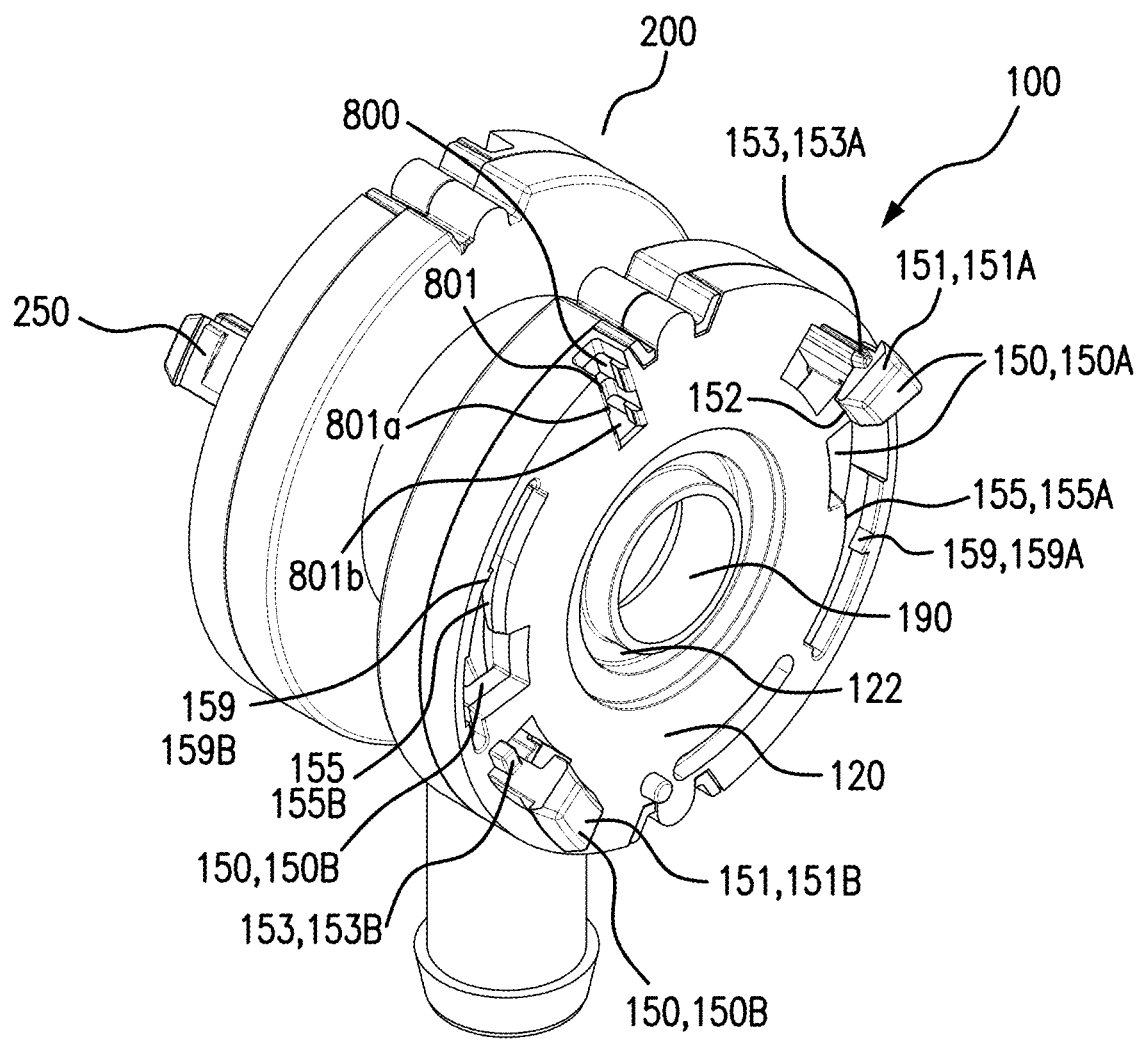
Figure 5C:
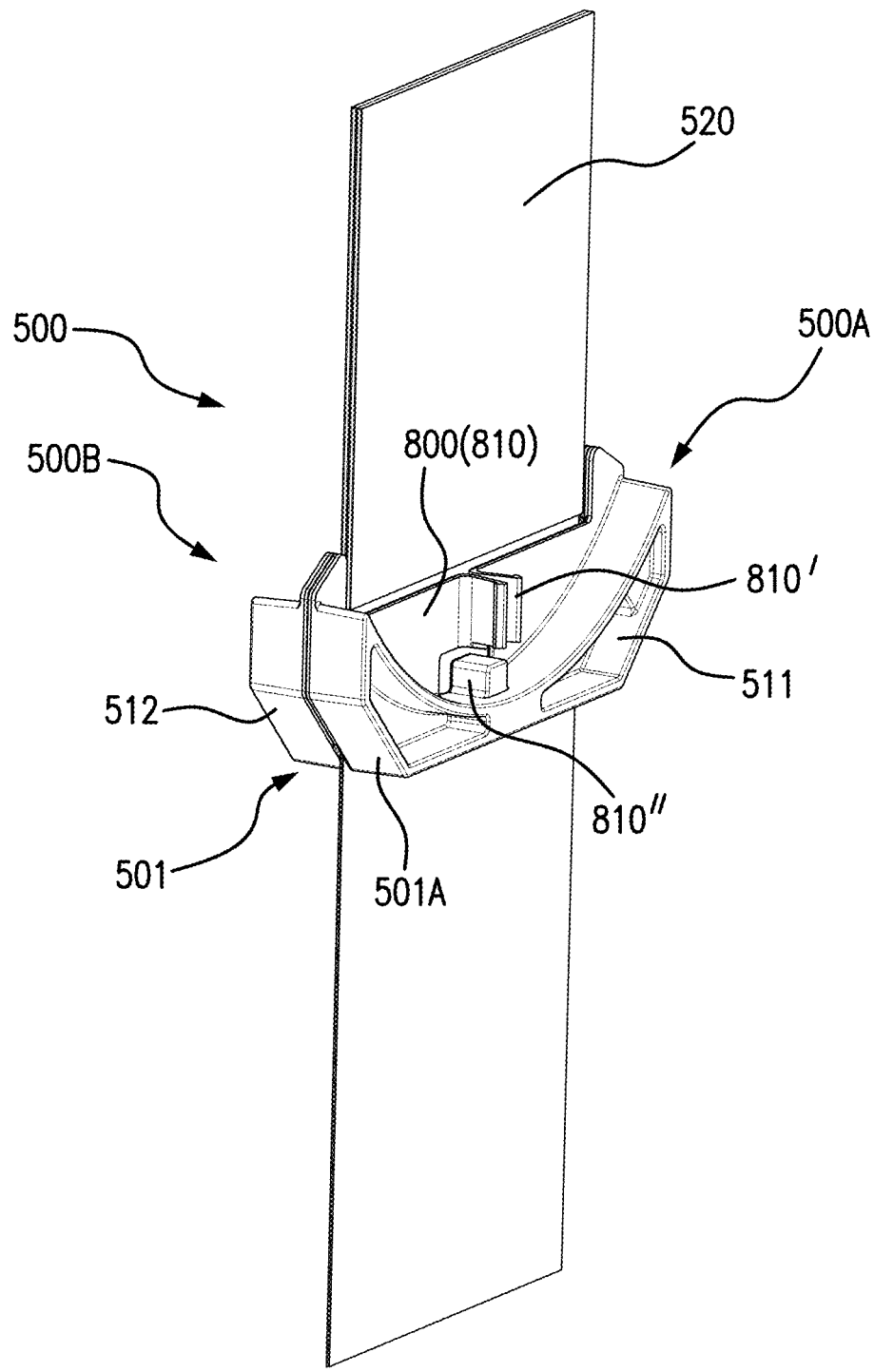
Figure 5D:
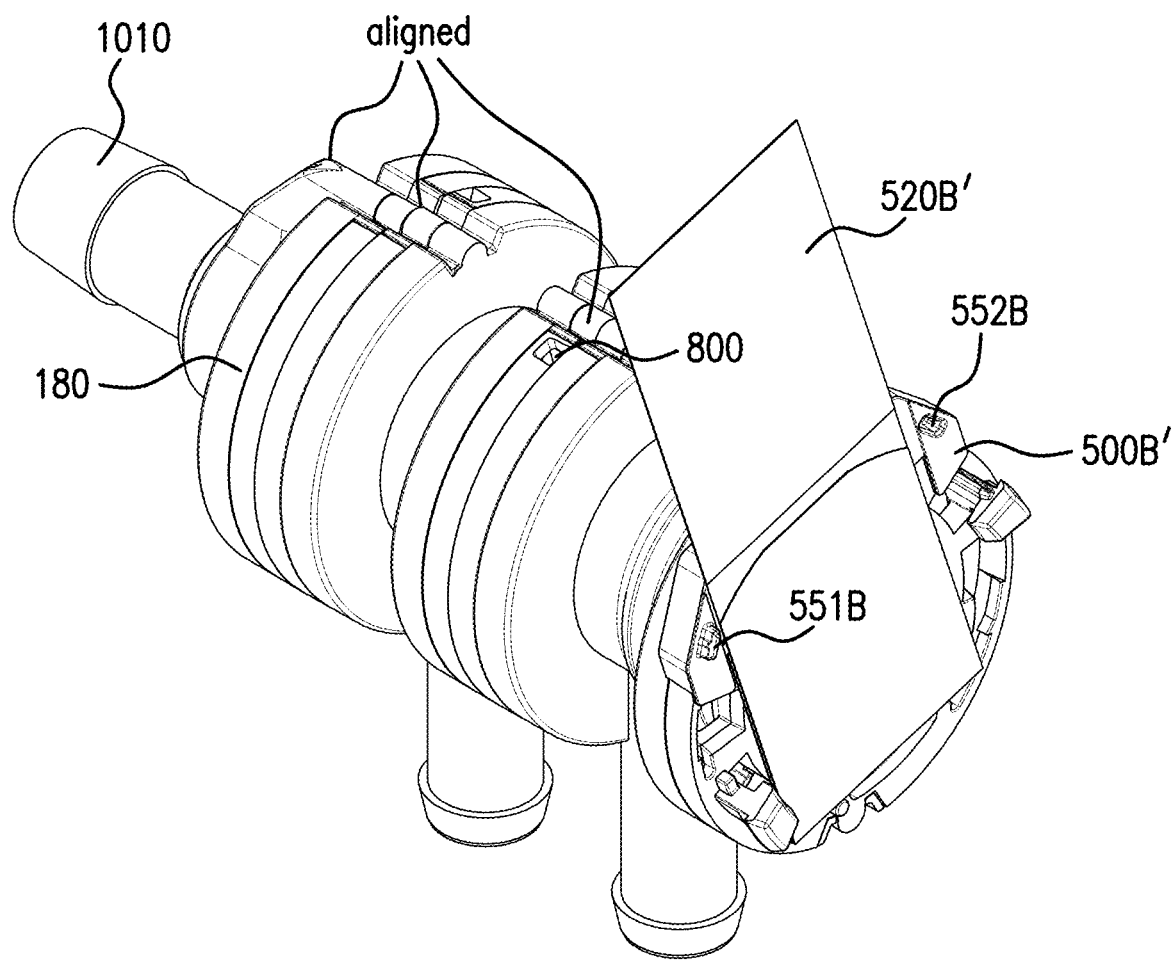
Figure 5E:
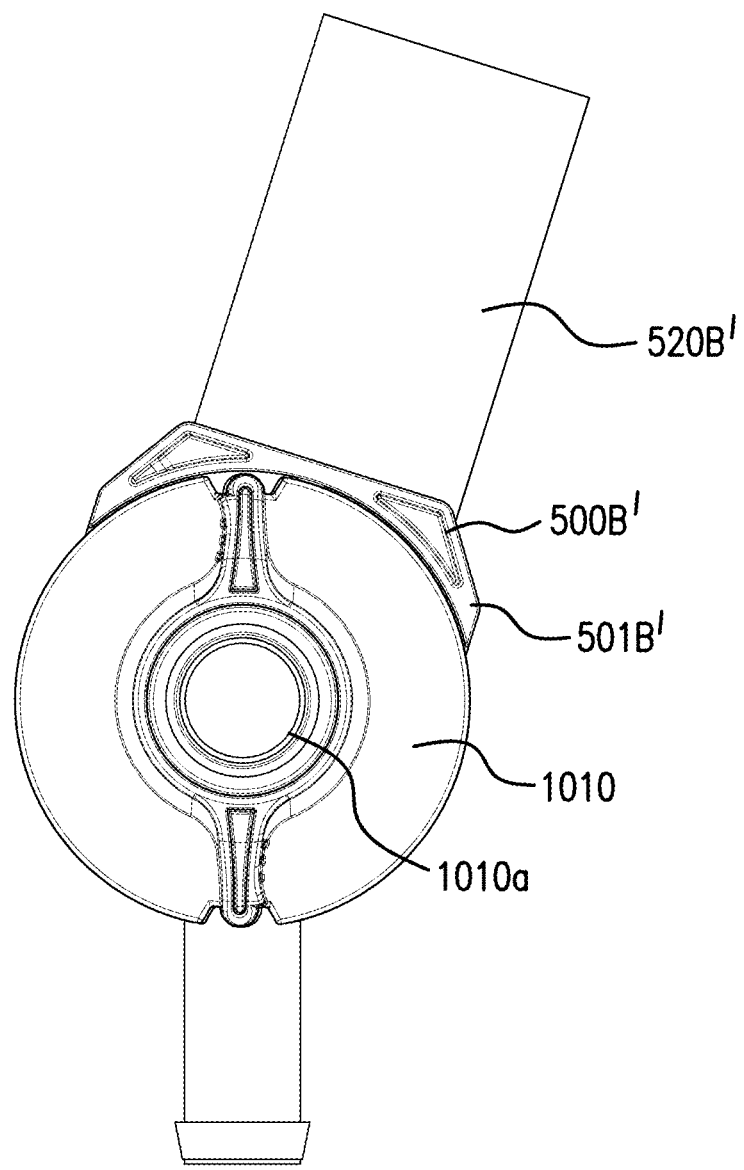

FIG. 5A is a drawing showing a rear perspective view of the first connector shown in FIG. 2A, also showing an anti-actuation subassembly and peel strip connected to the outer face of the hollow connector body; FIG. 5B is a drawing showing a rear perspective view of the first connector shown in FIG. 2B, also showing a second hollow connector outer body face with the anti-actuation subassemblies and peel strips removed from the outer body face; FIG. 5C is a drawing showing a perspective view of the anti-actuation subassembly of the anti-actuation assembly comprising a tab and a peelable strip in the connector arrangable between connectors, also showing another subassembly of the anti-actuation assembly used when first and second connector are connected; FIG. 5D is a drawing showing a rear perspective view of the joined first and second connectors shown in FIG. 2C, and FIG. 5E is a drawing showing a front view of the joined connectors shown in FIG. 5D.

Figure 1A:
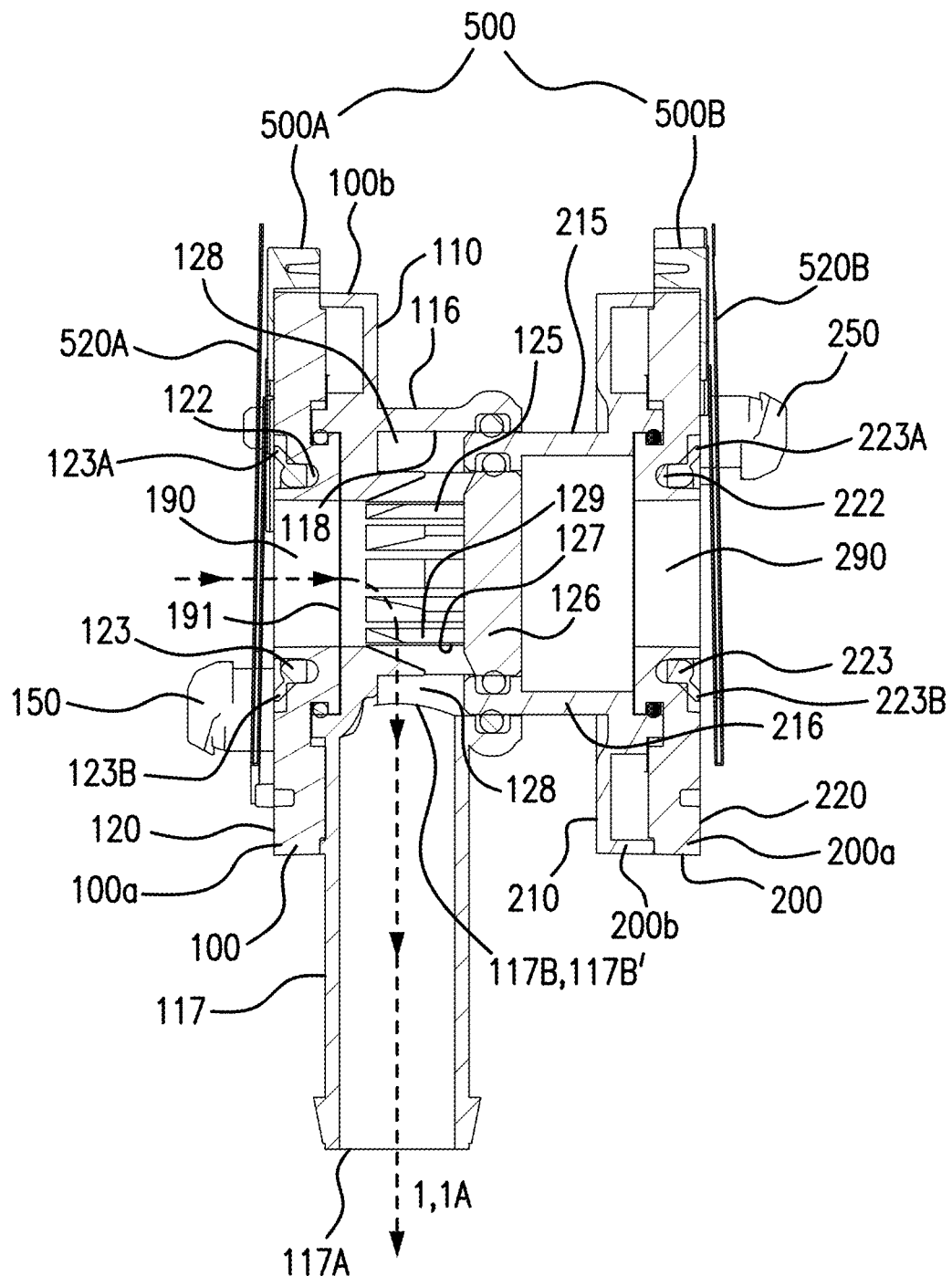
FIG. 1C shows is a drawing showing a cross-sectional view of first and second connectors according to an aspect of the invention joined, wherein the first connector is in the second collapsed position as shown in FIG. 1B, and the second connector is in the first expanded position, the second connector having an anti-actuation subassembly and a peel strip.
Figure 6A:
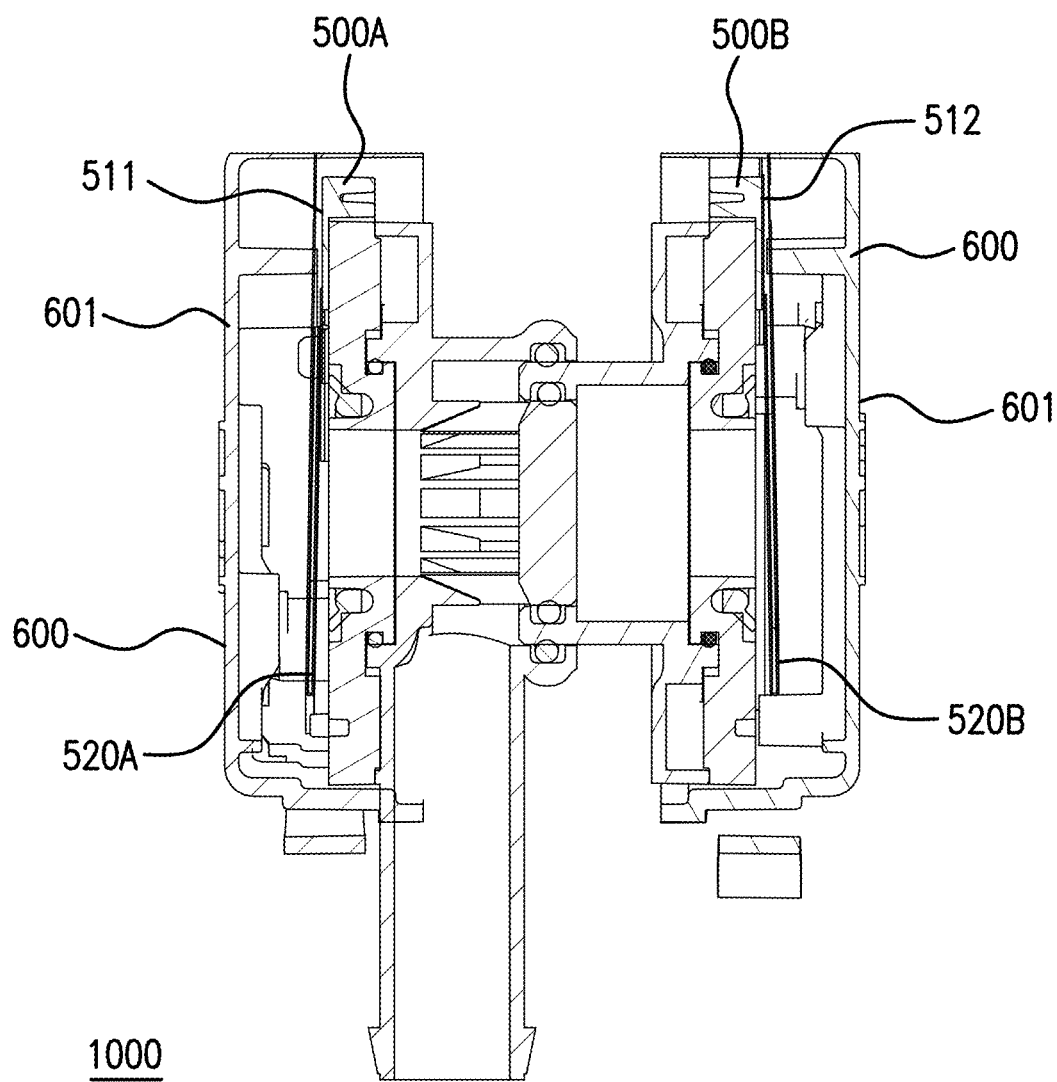
Figure 6B:
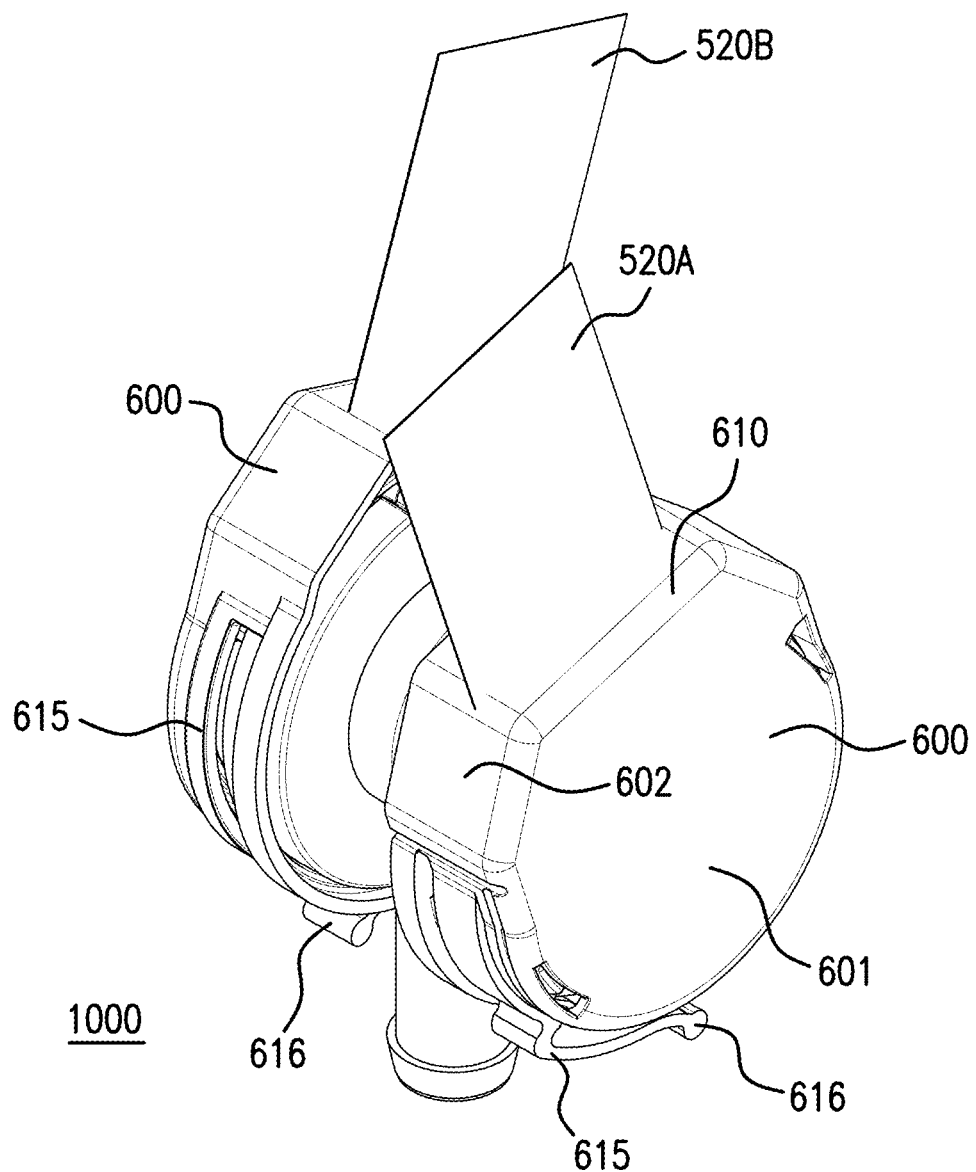

FIG. 6A is a drawing showing a cross-sectional view of a first connector assembly comprising the first connector shown in FIG. 1A according to an aspect of the invention (also showing integrally formed locking mechanisms and removable caps); FIG. 6B is a drawing showing a front perspective view of the first connector assembly shown in FIG. 6A.

DETAILED DESCRIPTION OF THE INVENTION

An aspect of the invention provides a connector comprising (a) a first hollow connector body having (i) a side wall with a hollow extension having an open first end and an open second end, the open second end forming a hollow extension aperture in the side wall; (ii) an outer face with an outer face aperture; and (iii) an inner face including a first projection, the first projection having an annular inner wall, surrounding a second projection, the second projection having a second projection annular outer wall, forming a space between the annular inner wall of the first projection and the annular outer wall of the second projection, the space having a bottom wall and an open end opposite the bottom wall; the second projection having a second projection annular inner wall and slots passing through the second projection inner wall and the second projection outer wall, a closed top end and an open second end providing the outer face aperture of the first hollow connector body, the outer face aperture being in fluid communication with the slots passing through the second projection inner wall and the second projection outer wall; (b) a second hollow connector body having an inner face including a hollow projection, the hollow projection having a wall having an inner surface and an outer surface and a top end with a planar annular surface; and an outer face; the second hollow connector body having an aperture passing through the inner face, the hollow projection and the outer face; wherein the connector has a first expanded position providing a first fluid flow path through the outer face aperture, the slots, the space between the annular inner wall of the first projection and the annular outer wall of the second projection, the side wall and the hollow extension of the first hollow connector body, when the top end with the planar annular surface of the second hollow connector body is a distance from the bottom wall of the space in the first hollow connector body; and, a second collapsed position providing a second fluid flow path through the outer face aperture, the slots, and the open end opposite the bottom wall of the first hollow connector body, and through the aperture passing through the inner face, the hollow projection and the outer face of the second hollow connector body, when the top end with the planar annular surface of the second hollow connector body contacts the bottom wall of the space of the first hollow connector body.

In a preferred aspect of the connector, the outer face of the first hollow connector body includes a first annular groove with a first resilient deformable annular seal arranged in the first annular groove around the outer face aperture; and the outer face of the second hollow connector body includes a second annular groove with a second resilient deformable annular seal arranged in the second groove around the outer face aperture.

In some aspects of the connectors, the first resilient annular seal in the first annular groove and the second resilient annular seal in the second annular groove each have a flexible lip.

In a preferred aspect of the connector, the outer face of the first hollow connector body includes an integrally formed locking mechanism; the integrally formed locking mechanism comprising at least one lug including a slot, and at least one ramp; and an anti-actuation assembly engagement portion comprising at least one recess and/or at least one protrusion; and, the outer face of the second hollow connector body includes an integrally formed locking mechanism; the integrally formed locking mechanism comprising at least one lug including a slot, and at least one ramp; and an anti-actuation assembly engagement portion comprising at least one recess and/or at least one protrusion.

In another aspect, a connector assembly is provided, comprising an aspect of the connector, further comprising a first removable cap, engaged with the first hollow connector body, wherein the removable anti-actuation assembly is interposed between the first removable cap and the first hollow connector body, the first removable cap covering the outer face of the first hollow connector body; and, a second removable cap, engaged with the second hollow connector body, wherein the removable anti-actuation assembly is interposed between the second removable cap and the second hollow connector body, the second removable cap covering the outer face of the second hollow connector body.

In accordance with yet another aspect of the invention, a method for making fluid connections is provided, the method comprising (A) placing a first connector comprising (a) a first hollow connector body having (i) a side wall with a hollow extension having an open first end and an open second end, the open second end forming a hollow extension aperture in the side wall; (ii) an outer face with an outer face aperture; and (iii) an inner face including a first projection, the first projection having an annular inner wall, surrounding a second projection, the second projection having a second projection annular outer wall, forming a space between the annular inner wall of the first projection and the annular outer wall of the second projection, the space having a bottom wall and an open end opposite the bottom wall; the second projection having a second projection annular inner wall and slots passing through the second projection inner wall and the second projection outer wall, a closed top end and an open second end providing the outer face aperture of the first hollow connector body, the outer face aperture being in fluid communication with the slots passing through the second projection inner wall and the second projection outer wall; (b) a second hollow connector body having an inner face including a hollow projection, the hollow projection having a wall having an inner surface and an outer surface and a top end with a planar annular surface; and an outer face; the second hollow connector body having an aperture passing through the inner face, the hollow projection and the outer face; wherein the connector has a first expanded position providing a first fluid flow path through the outer face aperture, the slots, the space between the annular inner wall of the first projection and the annular outer wall of the second projection, the side wall and the hollow extension of the first hollow connector body, when the top end with the planar annular surface of the second hollow connector body is a distance from the bottom wall of the space in the first hollow connector body; and, a second collapsed position providing a second fluid flow path through the outer face aperture, the slots, and the open end opposite the bottom wall of the first hollow connector body, and through the aperture passing through the inner face, the hollow projection and the outer face of the second hollow connector body, when the top end with the planar annular surface of the second hollow connector body contacts the bottom wall of the space of the first hollow connector body; in contact with: (B) a second connector comprising (a') a first hollow connector body having (i') a side wall with a hollow extension having an open first end and an open second end, the open second end forming a hollow extension aperture in the side wall; (ii') an outer face with an outer face aperture; and (iii') an inner face including a first projection, the first projection having an annular inner wall, surrounding a second projection, the second projection having a second projection annular outer wall, forming a space between the annular inner wall of the first projection and the annular outer wall of the second projection, the space having a bottom wall and an open end opposite the bottom wall; the second projection having a second projection annular inner wall and slots passing through the second projection inner wall and the second projection outer wall, a closed top end and an open second end providing the outer face aperture of the first hollow connector body, the outer face aperture being in fluid communication with the slots passing through the second projection inner wall and the second projection outer wall; (b') a second hollow connector body having an inner face including a hollow projection, the hollow projection having a wall having an inner surface and an outer surface and a top end with a planar annular surface; and an outer face; the second hollow connector body having an aperture passing through the inner face, the hollow projection and the outer face; wherein the connector has a first expanded position providing a first fluid flow path through the outer face aperture, the slots, the space between the annular inner wall of the first projection and the annular outer wall of the second projection, the side wall and the hollow extension of the first hollow connector body, when the top end with the planar annular surface of the second hollow connector body is a distance from the bottom wall of the space in the first hollow connector body; and, a second collapsed position providing a second fluid flow path through the outer face aperture, the slots, and the open end opposite the bottom wall of the first hollow connector body, and through the aperture passing through the inner face, the hollow projection and the outer face of the second hollow connector body, when the top end with the planar annular surface of the second hollow connector body contacts the bottom wall of the space of the first hollow connector body; the method further comprising contacting the outer face of the first hollow connector body of the second connector with the outer face of the second hollow connector body of the first connector to provide a first contacting position, twisting the first hollow connector body of the second connector and/or the of the second hollow connector body of the first connector to provide a second contacting position to provide an actuation position, placing the first connector in the second collapsed position, and placing the second connector in the first expanded position.

In a preferred aspect of the method, the method further includes passing fluid along the second fluid flow path through the first connector and through the first fluid flow path of the second connector. Aspects of methods for processing fluid can comprise passing the fluid through any number of connected connectors and/or connector assemblies.

Advantageously, two or more connectors and/or connector assemblies according to aspects of the invention can be connected to extend the number of operations (multiple sterile connections through the same initial connection). As a result, the number of possible leak points in the flow path are reduced (no need to replace manifold, fewer junctions for the same given number of connections), also reducing the size of complexity of the overall manifold. An operator has the choice to use as many connector assemblies as needed for the process, without relying upon complex arrangements of connectors, conduits, T- and Y-connectors, and external hardware such as valves and/or controllers.

Preferably, the connector or connector assembly is a genderless connector assembly, i.e., not requiring male and female connections. Advantageously, a connector or connector assembly can be connected to another connector or connector assembly, for example, a connector assembly as described herein, or as described in U.S. Pat. No. 10,247, 342.

Aspects of the invention are also suitable for single use technology (SUT) applications.

Each of the components of the invention will now be described in more detail below, wherein like components have like reference numbers.

Figure 1B:
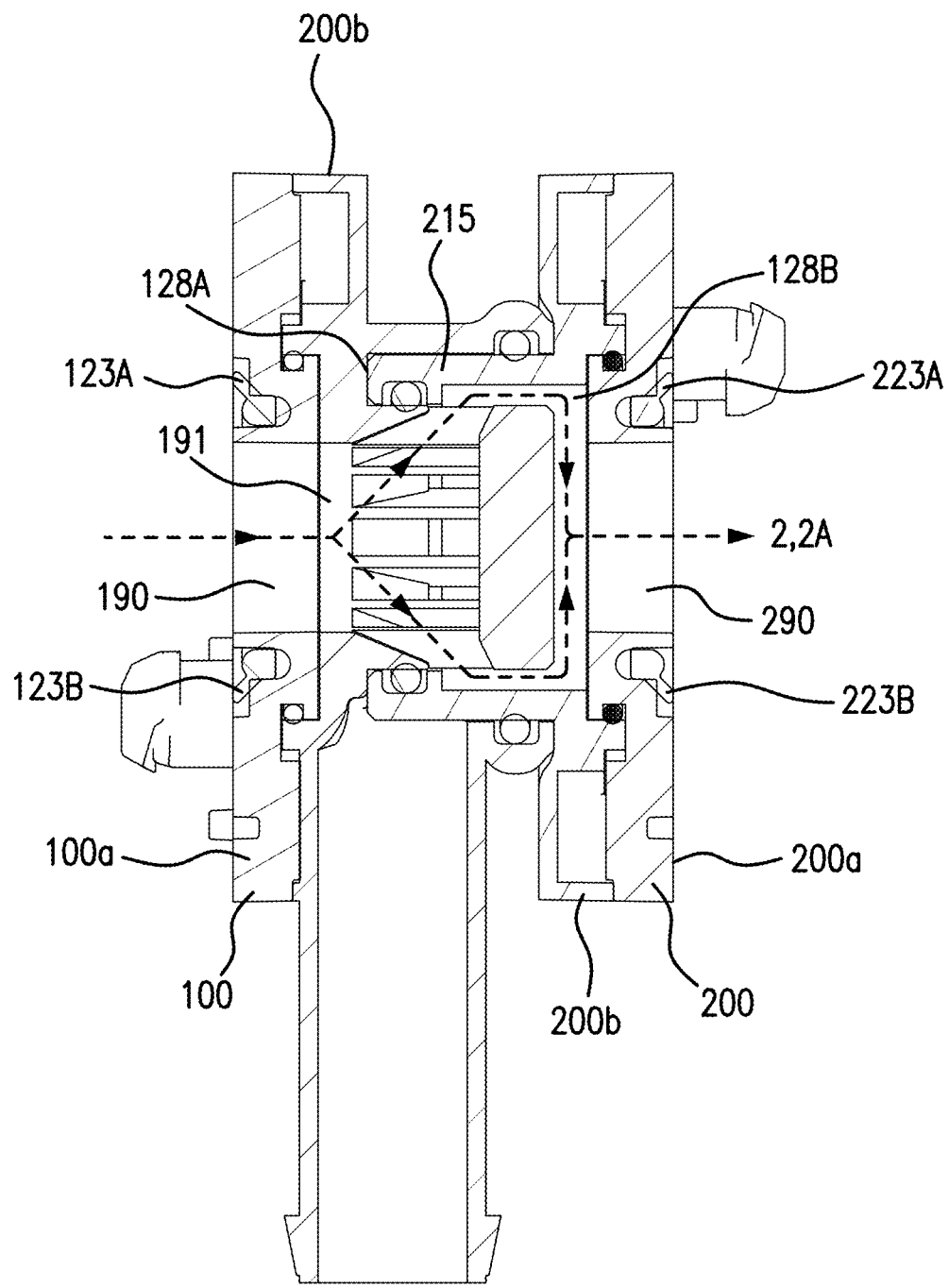

FIGS. 1A and 1B show an aspect of a connector 1000 comprising (a) a first hollow connector body 100 having (i) a side wall 116 with a hollow extension 117 having an open first end 117A and an open second end 117B, the open second end forming a hollow extension aperture 117B' in the side wall; (ii) an outer face 120 with an outer face aperture 190, the outer face including an annular groove 122 (surrounding the aperture 190) receiving a resilient seal 123 (preferably, a resilient deformable seal including a lip 123A in a chamber 123B; see also, FIG. 3C), and (iii) an inner face 110 including a first projection 115, the first projection having an annular inner wall 118 (see also, FIG. 3C), surrounding a second projection 125, the second projection having a second projection annular outer wall 127, forming a space 128 between the annular inner wall of the first projection and the annular outer wall of the second projection, the space having a bottom wall 128A and an open end 128B opposite the bottom wall (see also, FIG. 3C), the second projection having a second projection annular inner wall 129 and slots 129A passing through the second projection annular inner wall 129 and the second projection annular outer wall 127, a closed top end 126, and an open second end 191 providing the outer face aperture 190 of the first hollow connector body, the outer face aperture being in fluid communication with the slots 129A passing through the second projection inner wall and the second projection outer wall; (b) a second hollow connector body 200 having an inner face 210 including a hollow projection 215, the hollow projection having a annular wall 216 having an annular inner surface 219 and an annular outer surface 217 and a top end 226 with a planar annular surface 226A (see also, FIG. 4); and an outer face 220; the second hollow connector body having an aperture 290 passing through the inner face 220, the inner face including an annular groove 222 (surrounding the aperture 290) receiving a resilient seal 223 (preferably, a resilient deformable seal including a lip 223A in a chamber 223B; see also, FIG. 4), the hollow projection 215 and the outer face 210; wherein the connector has a first expanded position 1 providing a first fluid flow path 1A (see also, FIG. 2A) through the outer face aperture, the slots, the space between the annular inner wall of the first projection and the annular outer wall of the second projection, the side wall and the hollow extension of the first hollow connector body 100, when the top end with the planar annular surface of the second hollow connector body 200 is a distance from the bottom wall 128A of the space 128 in the first hollow connector body; and, a second collapsed position 2 providing a second fluid flow path 2A (see also, FIG. 2B) through the outer face aperture 190, the slots 129A, and the open end 128B opposite the bottom wall 128A of the first hollow connector body 100, and through the aperture 290 passing through the inner face 210, the hollow projection 215 and the outer face 220 of the second hollow connector body 200, when the top end 226 with the planar annular surface 226A of the second hollow connector body 200 contacts the bottom wall 128A of the space 128 of the first hollow connector body 100.

In FIG. 1A, the first and second hollow connector bodies are each illustrated as two parts (100a, 100b; 200a, 200b) joined together, but they can each be single piece integral structures.

Preferably, as shown in FIGS. 3C and 4, annular inner wall 118, and annular inner surface 219 each include, respectively, a groove 121a, 221a, containing an annular resilient seal 121b, 221b, such as an o-ring. In some aspects, the resilient seals have outer flexible lips.

The bottom faces 120, 220 of the collector bodies 100, 200 each include a locking mechanism 150, 250 for coupling to additional connectors and connector assemblies, e.g. wherein a second hollow collector body 200 of one connector or connector assembly is connected to a first hollow collector body 100 of another connector or connector assembly in a first contacting position, and placed in an actuation position after removing an removable anti-actuation assembly 500 comprising a peel strip 520 (preferably including peel strips 520A, 520B), and the second hollow connector body of the first connector and/or the first hollow connector body of the second connector are twisted such that the respective resilient seals seal against the hollow connector bodies in a second contacting position, comprising an actuation position.

Preferably, using FIGS. 1A, 5A, and 6A for reference, an anti-actuation assembly 500 comprises first anti-actuation subassembly 500A comprising a subassembly tab 501A including a first surface 511, and a first peel strip 520A; and, a second anti-actuation subassembly 500B comprising a subassembly tab 501B including the second surface 512, and a second peel strip 520B.

Figure 1C:
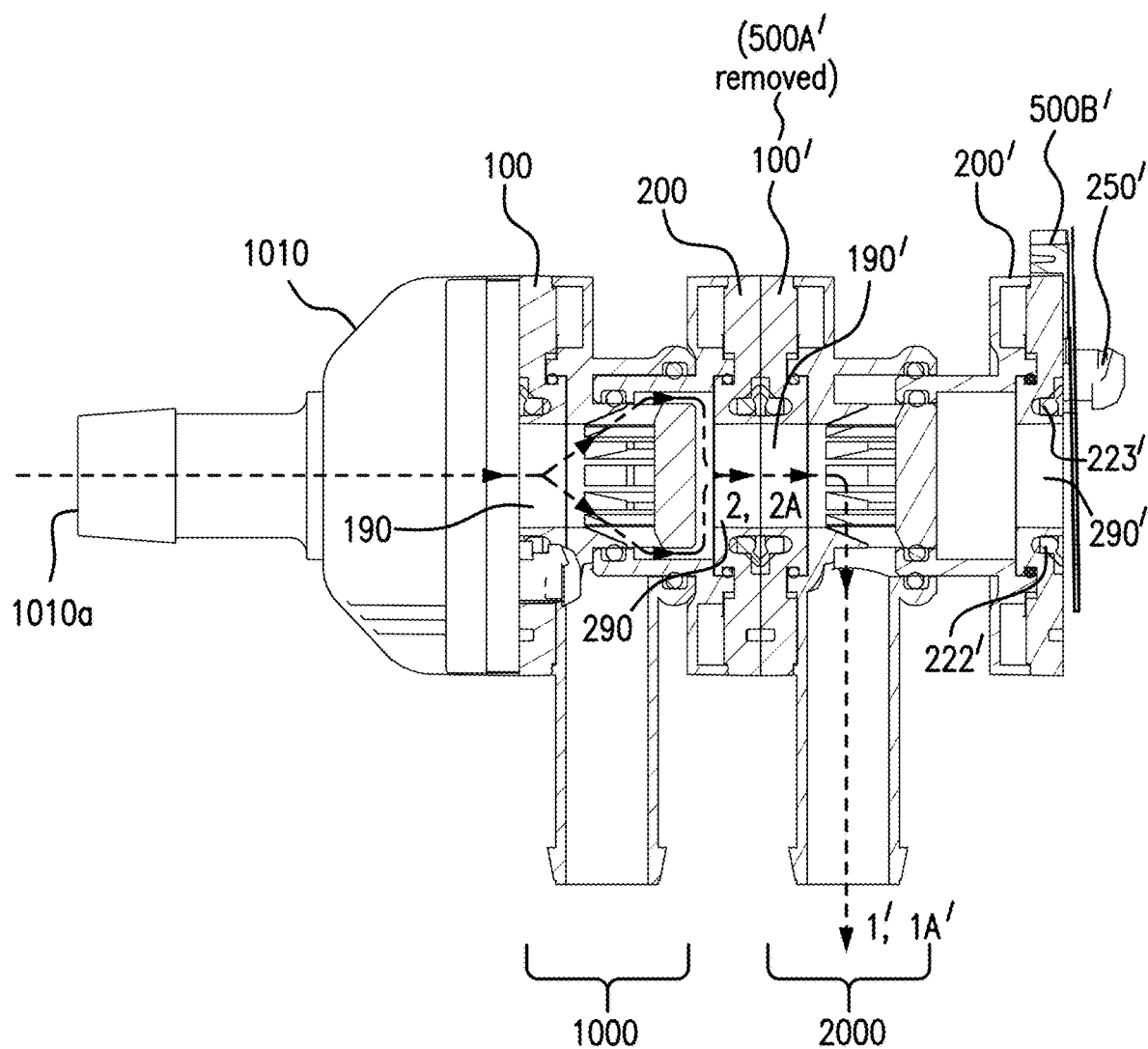

Using FIG. 1C for reference, showing part of first connector assembly 1000 and part of an additional (second) connector assembly 2000 (the first and second connector assemblies having the same structures, wherein the second connector assembly 2000 includes "'" to label structures corresponding to those in first connector assembly 1000), first anti-actuation subassembly 500A is removed from first hollow body 100 before providing an actuation position through inlet nipple 1010 (having inlet port 1010a), second anti-actuation subassembly 500A is removed from second hollow body 200, and first anti-actuation subassembly 500A' is removed from second connector first hollow body 100' before providing an actuation position between second hollow connector body 200 and first hollow connector body 100', placing the first connector in the second collapsed position and the second connector in the first expanded position and passing fluid along the second fluid flow path through the first connector and through the first fluid flow path of the second connector.

Preferably, using FIGS. 1A, 5A, and 6 for reference, if desired, each subassembly can comprise a keying arrangement comprising at least one protrusion and at least one recess so that the first anti-actuation subassembly and the second anti-actuation subassembly can be mated together when a first hollow connector body of one connector or connector assembly and a second hollow connector body of another connector or connector assembly contact each other in the first position. For example, as shown in FIG. 5A, subassembly tab 501A has a second surface 521A including a keying arrangement 550A comprising a protrusion 551A and a recess 552A, and corresponding subassembly tab 501B would have the same structure, i.e., a second surface including a keying arrangement comprising a protrusion and a recess, wherein protrusion 551A can be mated with the recess in subassembly 501B, and the protrusion in subassembly 501B and be mated with recess 551A. Advantageously, this allows the operator to pull either or both tabs 501A, 501B and/or either or both peelable strips 520A, 520B and remove the anti-actuation assembly from the connectors or connector assembles, so that the hollow connector bodies can be placed in the actuation position. If desired, the tab can include a pull ring.

In some aspects, the integrally formed locking mechanism and anti-actuation assemblies and their operation can be as described in U.S. Pat. No. 10,247,342.

If desired, the connector assembly can comprise an alignment arrangement for mating the anti-actuation assembly with the first connector hollow body and the second hollow connector body, the alignment arrangement comprising protrusions and recesses; wherein the first and second surfaces of the anti-actuation assembly, the first hollow connector bottom face, and the second hollow connector bottom face each have at least one protrusion and/or at least one recess, such that the first surface of the anti-actuation assembly mates with the first hollow connector first body end, and the second surface of the anti-actuation assembly mates with the second hollow connector first body end.

For example, in the aspect shown in FIGS. 5B, and 5C, the connector further comprises an alignment arrangement 800, including a recess 801 in the outer face of the first hollow connector body (illustrated recess shown with 2 slots, 801a, 801b), and a protrusion 810 (shown as having 2 snap hooks 810' and a pin 810") on the first surface 511 of the anti-actuation tab 501, the protrusion being engageable with the recess 801 (wherein the second connector hollow body has the same structure). As discussed below, in aspects including pins, the engagement of the pins with the recesses further reduces flexing/movement when the subassemblies are engaged with the respective hollow bodies.

In some aspects, first and second collector assemblies 1000, 2000 have identical structures and are coupled to each other by respective identical locking mechanisms (see, for example, FIG. 1C). However, in other aspects, a collector assembly according to an aspect of the invention can be coupled to a different collector assembly, e.g., as disclosed in U.S. Pat. No. 10,247,342.

Any number of connectors and/or connector assemblies can be joined, and each additionally joined connector or connector assembly will be initially utilized with the respect to the first expanded position, and the first fluid flow path, via the second collapsed position and the second fluid flow path through the connector or connector assembly connected to the new (additional) connector or connector assembly. Thus, for example, using the aspect shown in FIGS. 1C and 2C for reference, an additional (e.g., third) connector can be connected to the outer face 200' of second connector 2000, and, after removing the peel strips, placing the hollow bodies in the actuation position, subsequently receiving fluid along the second fluid flow path from the second connector after the second connector is in the second collapsed position and the third collector is in the first expanded position, passing fluid along the first flow path through the third connector.

The hollow connector bodies 100, 200 may be coupled to corresponding hollow bodies of other connectors or connector assemblies at their bottom faces 120, 220 by respective locking mechanisms (first locking mechanism 150; second locking mechanism 250). Using FIG. 5B for reference, showing first connector body 100 first locking mechanism 150, wherein the second connector body 200 second locking mechanism 250 would have the corresponding structures, the locking mechanism comprising a lug 151 extending above the face, the lug including a slot 152 and a guide 153, a recess 154, and a ramp 155 extending below the face, and an arm 159. In the embodiment illustrated in FIG. 5B the first connector body 100 includes first locking mechanisms 150A, 150B, including lugs 151A, 151B, slots 152A, 152B, guide 153A, 153B, ramps 155A, 155B, and arms 159A, 159B. The locking mechanisms are integrally formed with the bodies, and as such, does not move separately from the rest of the body when the body moves from the first position to the second position.

After an anti-actuation assembly 500 is removed, either or both of the hollow connector bodies can be rotated from a first position such that the ramp(s) of the locking mechanism (s) of one hollow connector body engages with the slot(s) in the lug(s) of the locking mechanism(s) of the other hollow connector body, until the hollow bodies are in a second (actuation) position. Once the bodies are in the actuation position, the interiors of the connector bodies fluidly communicate with one another, preferably, in a sterile manner free of any external contamination.

The hollow bodies can be coupled to each other, including using the locking mechanisms and rotation from the first contacting position to the second contacting (actuation or activation) position, as disclosed in U.S. Pat. No. 10,247, 342.

Optionally, (a) the surface of the ramp and the surface of the slot that will contact the surface of the ramp have initial angles, and then level, such that the lugs stop on a level surface, providing a desired amount of pressure on the main bodies of the seals, when the connector bodies are in the actuation position, and/or (b) the corresponding locking mechanisms have corresponding arms that lock the lug guides into the recesses once the lugs have passed, retaining the lugs in the actuation position, to prevent disconnection.

To enhance the sterility of the interiors of the connector bodies, peel strips (seal layers) are preferably arranged to cover the openings at the first ends of the connector bodies. The peel strips may be variously configured. Typically, the peel strip(s) are joined (e.g., welded, trapped, or clamped) to the anti-actuation assembly tab(s) and/or the faces of the hollow connector bodies. Preferably, peel strips are joined to the respective subassembly tabs and the hollow connector body faces (also covering the seals and contacting the seal lips). For many embodiments, the peel strip(s) may also cover all or at least a portion of the face seals without being joined to the seals. For example, each peel strip may completely cover at least the seal closest to the openings. The peel strip may not be joined to the seals themselves but may be joined to the surface of the face surrounding each seal.

The peel strip may be made from an impermeable material or a permeable material that resists the passage of contaminants, including biological containments. These materials include, but are not limited to, elastomeric sheets, polymeric films, and metal foils, e.g., aluminum foil, any of which may further include a reinforcing material. Further, the peel strip may be coated and/or impregnated with a biocide. Preferably, the peel strip is a sterile porous or microporous membrane, allowing steam to pass through during autoclaving, in some aspects having a minimum tensile strength of about 60 N.

Any of numerous seals may be provided on the face, including, for example, gaskets, resilient sealing members, or O-rings. Preferably, the seal comprises a soft rubber or thermoplastic elastomer (TPE) (e.g., about 50 to about 65 shore A). The flexible seal lips 123A, 223A can assist in preventing environmental contamination from entering the connector assembly when the anti-actuation assembly is removed. Since the lips can flex and spring, the peel strips can be removed with reduced force, and the lips quickly close the gap. As the hollow bodies are moved (e.g., twisted) into the actuation position, the flexible lips (that are preferably narrow) quickly fold out of the way into a recess 123B, 223B in each body wherein both the lips and the seal bodies (seal lozenges) contact each other, providing a more robust face seal, and the contact between the lozenges provides a face to face seal, preventing fluid leaks even under increases pressures (e.g., pressures up to about 4 barg).

If desired, the hollow connector bodies can external connector body alignment indicators (e.g., 900a, 900b, 900c) such that the alignment indicators do not align the hollow connector bodies are in the first connecting position, and they align when the hollow connector bodies are in the second (actuation (or activating)) position.

To prevent inadvertent removal of or damage to the peel strips, each connector body may further comprise a removable cap which covers at least a substantial portion of the peel strip and the first end of the connector body. The cap can be fitted to the connector body at the first end, for example, by a friction fit or a snap fit, and may have any of a wide variety of configurations. For example, as shown in FIGS. 6A and 6B, each cap 600 (cap 700 on the second connector assembly will have the same structures) may have a rigid top 601 which protects at least part of the peel strip and a skirt 602 which fits along the rim of the connector body 100, 200. The cap 600 may also include handle 610 as part of the skirt, or which extends axially below the skirt 602. Preferably, as shown in FIG. 6B, the cap includes a tear strip 615 having a tear strip handle 616 allowing the operator to grasp the tear strip handle and tear the tear strip, allowing the cap to be more easily removed from the connector body. The peel strip 520 (520A) may be bent axially under the handle 610 and the handle may extend along all or at least a portion of the peal strip 520 (520A). The handle, tear strip, and/or tear strip handled may be used to lift the cap 600 off of the connector body 100 and may also prevent inadvertent manipulation of the anti-actuation assembly tab 501 and/or peel strip.

The components of the connector assembly can be sterilized as is known in the art (e.g., autoclaved, gamma irradiated, etc.)

The components of the connector assembly may be formed from a wide variety of materials. For example, one or more of any one of the following: hollow connector body, hollow tube, connector body cover, locking mechanism, tab, and cap, may be made from any metallic material and/or polymeric material which is compatible with the fluid that will flow through the connector assembly. Preferably, the connector bodies, hollow tubes, the locking mechanisms, and the caps are made from polymeric material, and the polymeric material may include, but is not limited to, one or more of a polycarbonate, polypropylene, polystyrene, polyvinyl chloride, polyethersulphone, polyvinylidene fluoride, or polysulphone. For some embodiments, a transparent or translucent polymeric material may be selected. Typically, the hollow bodies, hollow tubes, tabs, and connector body covers are formed from a rigid injection molded plastic, preferably a BPA-free plastic, such as polyethersulfone (PES), polycarbonate (PC), polysulfone (PSU), and polybutylene terephthalate (PBT), and the cap is made from a low density injection molded plastic such as TPE or polypropylene (PP).

The components may be fabricated in a variety of ways, including molding, machining, pressing, and stamping, and may be fashioned into subassemblies.

Additionally, or alternatively, some components according to aspects of the invention can be monolithic, for example, manufactured via additive manufacturing (sometimes referred to as "additive layer manufacturing" or "3D printing"). They are typically formed by repeated depositions of a metal powder bound together with an activatable binder (e.g., binder jetting, sometimes referred to as "drop on powder"), typically followed by agglomerating the powder, e.g., by sintering. Some components can be manufactured together via additive manufacturing in a continuous operation at substantially the same time.

Any suitable additive manufacturing equipment can be used, and a variety of production 3D printers are suitable and commercially available.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred aspects of this invention are described herein, including the best mode known to the inventors for carrying out the invention. Variations of those preferred aspects may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A connector comprising
(a) a first hollow connector body having
    (i) a side wall with a hollow extension having an open first end and an open second end, the open second end forming a hollow extension aperture in the side wall;
    (ii) an outer face with an outer face aperture; and
    (iii) an inner face including a first projection, the first projection having an annular inner wall, surrounding a second projection,
        the second projection having a second projection annular outer wall, forming a space between the annular inner wall of the first projection and the annular outer wall of the second projection, the space having a bottom wall and an open end opposite the bottom wall;
        the second projection having a second projection annular inner wall and slots passing through the second projection inner wall and the second projection outer wall, a closed top end and an open second end providing the outer face aperture of the first hollow connector body, the outer face aperture being in fluid communication with the slots passing through the second projection inner wall and the second projection outer wall;
(b) a second hollow connector body having an inner face including a hollow projection, the projection having a wall having an inner surface and an outer surface and a top end with a planar annular surface; and
an outer face; the second hollow connector body having an aperture passing through the inner face, the hollow projection and the outer face;
    wherein the outer face of the first hollow connector body includes a first annular groove with a first resilient deformable annular seal arranged in the first annular groove around the aperture; and the outer face of the second hollow connector body includes a second annular groove with a second resilient deformable annular seal arranged in the second groove around the aperture;
    wherein the connector has a first expanded position providing a first fluid flow path through the outer face aperture, the slots, the space between the annular inner wall of the first projection and the annular outer wall of the second projection, the side wall and the hollow extension of the first hollow connector body, when the top end with the planar annular surface of the second hollow connector body is a distance from the bottom wall of the space in the first hollow connector body;
    and,
    a second collapsed position providing a second fluid flow path through the outer face aperture, the slots, and the open end opposite the bottom wall of the first hollow connector body, and through the aperture passing through the inner face, the hollow projection and the outer face of the second hollow connector body, when the top end with the planar annular surface of the second hollow connector body contacts the bottom wall of the space of the first hollow connector body.

2. The connector of claim 1, wherein the first resilient annular seal in the first annular groove and the second resilient annular seal in the second annular groove each have a flexible lip.

3. The connector of claim 1, wherein the outer face of the first hollow connector body includes an integrally formed locking mechanism; the integrally formed locking mechanism comprising at least one lug including a slot, and at least one ramp; and an anti-actuation assembly engagement portion comprising at least one recess and/or at least one protrusion; a removable anti-actuation assembly comprising at least one peel strip, and at least one recess and/or at least one protrusion, the at least one recess and/or at least one protrusion being engaged with the anti-actuation assembly engagement portion of the first hollow connector body;

and, a first removable cap, engaged with the first hollow connector body, wherein the removable anti-actuation assembly is interposed between the first removable cap and the first hollow connector body, the first removable cap covering the outer face of the first hollow connector body; and, the outer face of the second hollow connector body includes an integrally formed locking mechanism; the integrally formed locking mechanism comprising at least one lug including a slot, and at least one ramp; and an anti-actuation assembly engagement portion comprising at least one recess and/or at least one protrusion; a removable anti-actuation assembly comprising at least one peel strip, and at least one recess and/or at least one protrusion, the at least one recess and/or at least one protrusion being engaged with the anti-actuation assembly engagement portion of the second hollow connector body; and, a second removable cap, engaged with the second hollow connector body, wherein the removable anti-actuation assembly is interposed between the second removable cap and the second hollow connector body, the second removable cap covering the outer face of the second hollow connector body.

4. The connector of claim 2, wherein the outer face of the first hollow connector body includes an integrally formed locking mechanism; the integrally formed locking mechanism comprising at least one lug including a slot, and at least one ramp; and an anti-actuation assembly engagement portion comprising at least one recess and/or at least one protrusion; a removable anti-actuation assembly comprising at least one peel strip, and at least one recess and/or at least one protrusion, the at least one recess and/or at least one protrusion being engaged with the anti-actuation assembly engagement portion of the first hollow connector body; and, a first removable cap, engaged with the first hollow connector body, wherein the removable anti-actuation assembly is interposed between the first removable cap and the first hollow connector body, the first removable cap covering the outer face of the first hollow connector body; and, the outer face of the second hollow connector body includes an integrally formed locking mechanism; the integrally formed locking mechanism comprising at least one lug including a slot, and at least one ramp; and an anti-actuation assembly engagement portion comprising at least one recess and/or at least one protrusion; a removable anti-actuation assembly comprising at least one peel strip, and at least one recess and/or at least one protrusion, the at least one recess and/or at least one protrusion being engaged with the anti-actuation assembly engagement portion of the second hollow connector body; and, a second removable cap, engaged with the second hollow connector body, wherein the removable anti-actuation assembly is interposed between the second removable cap and the second hollow connector body, the second removable cap covering the outer face of the second hollow connector body.

5. A method for making fluid connections, the method comprising (A) placing a first connector comprising (a) a first hollow connector body having (i) a side wall with a hollow extension having an open first end and an open second end, the open second end forming a hollow extension aperture in the side wall; (ii) an outer face with an outer face aperture; and (iii) an inner face including a first projection, the first projection having an annular inner wall, surrounding a second projection, the second projection having a second projection annular outer wall, forming a space between the annular inner wall of the first projection and the annular outer wall of the second projection, the space having a bottom wall and an open end opposite the bottom wall; the second projection having a second projection annular inner wall and slots passing through the second projection inner wall and the second projection outer wall, a closed top end and an open second end providing the outer face aperture of the first hollow connector body, the outer face aperture being in fluid communication with the slots passing through the second projection inner wall and the second projection outer wall; (b) a second hollow connector body having an inner face including a hollow projection, the hollow projection having a wall having an inner surface and an outer surface and a top end with a planar annular surface; and an outer face; the second hollow connector body having an aperture passing through the inner face, the hollow projection and the outer face; wherein the connector has a first expanded position providing a first fluid flow path through the outer face aperture, the slots, the space between the annular inner wall of the first projection and the annular outer wall of the second projection, the side wall and the hollow extension of the first hollow connector body, when the top end with the planar annular surface of the second hollow connector body is a distance from the bottom wall of the space in the first hollow connector body; and, a second collapsed position providing a second fluid flow path through the outer face aperture, the slots, and the open end opposite the bottom wall of the first hollow connector body, and through the aperture passing through the inner face, the hollow projection and the outer face of the second hollow connector body, when the top end with the planar annular surface of the second hollow connector body contacts the bottom wall of the space of the first hollow connector body;

in contact with:

(B) a second connector comprising (a') a first hollow connector body having (i') a side wall with a hollow extension having an open first end and an open second end, the open second end forming a hollow extension aperture in the side wall; (ii') an outer face with an outer face aperture; and (iii') an inner face including a first projection, the first projection having an annular inner wall, surrounding a second projection, the second projection having a second projection annular outer wall, forming a space between the annular inner wall of the first projection and the annular outer wall of the second projection, the space having a bottom wall and an open end opposite the bottom wall; the second projection having a second projection annular inner wall and slots passing through the second projection inner wall and the second projection outer wall, a closed top end and an open second end providing the outer face aperture of the first hollow connector body, the outer face aperture being in fluid communication with the slots passing through the second projection inner wall and the second projection outer wall; (b') a second hollow connector body having an inner face including a hollow projection, the hollow projection having a wall having an inner surface and an outer surface and a top end with a planar annular surface; and an outer face; the second hollow connector body having an aperture passing through the inner face, the hollow projection and the outer face; wherein the connector has a first expanded position providing a first fluid flow path through the outer face aperture, the slots, the space between the annular inner wall of the first projection and the annular outer wall of the second projection, the side wall and the hollow extension of the first hollow connector body, when the top end with the planar annular surface of the second hollow connector body is a distance from the bottom wall of the space in the first hollow connector body; and, a second collapsed position providing a second fluid flow path through the outer face aperture, the slots, and the open end opposite the bottom wall of the first hollow connector body, and through the aperture passing through the inner face, the hollow projection and the outer face of the second hollow connector body, when the top end with the planar annular surface of the second hollow connector body contacts the bottom wall of the space of the first hollow connector body;

the method further comprising contacting the outer face of the first hollow connector body of the second connector with the outer face of the second hollow connector body of the first connector to provide a first contacting position, twisting the first hollow connector body of the second connector and/or the of the second hollow connector body of the first connector to provide a second contacting position to provide an actuation position, placing the first connector in the second collapsed position, and placing the second connector in the first expanded position.

6. The method of claim 5 further comprising passing fluid along the second fluid flow path through the first connector and through the first fluid flow path of the second connector.

* * * * *